United States Patent [19]

Ohnishi et al.

[11] 4,447,437
[45] May 8, 1984

[54] PHARMACEUTICAL COMPOSITION AND METHOD FOR TREATMENT OF PEPTIC ULCER

[75] Inventors: Haruo Ohnishi; Chihiro Itoh, both of Chiba; Ei Mochida, Tokyo, all of Japan

[73] Assignee: Mochida Pharmaceutical Co., Ltd., Tokyo, Japan

[21] Appl. No.: 381,324

[22] Filed: May 24, 1982

[30] Foreign Application Priority Data

Jun. 3, 1981 [JP] Japan ................................ 56-140553

[51] Int. Cl.³ ............................................ A61K 31/44
[52] U.S. Cl. .................................................. 424/263
[58] Field of Search ......................................... 424/263

[56] References Cited

U.S. PATENT DOCUMENTS 4,002,632  1/1977  van der Burg ................. 260/290 H

OTHER PUBLICATIONS

*Chemical Abstracts,* vol. 83 (1975), 193278s.
The Pharm. Basis of Ther., The MacMillan Co., N.Y., pp. 540–542.

*Primary Examiner*—Frederick E. Waddell
*Attorney, Agent, or Firm*—Parkhurst & Oliff

[57] ABSTRACT

A pharmaceutical composition for the treatment of peptic ulcer which contains 2-N-methyl-1,2,3,4-tetrahydro-9H-dibenzo-[a,e]-pyridino[3,4-c]cycloheptatriene (MO-8282) or its pharmaceutically acceptable salt as an active ingredient in association with a pharmaceutically acceptable carrier, and a method for treating peptic ulcer by administering the said compound, MO-8282. The said compound exhibits high efficacy in the treatment of peptic ulcer and has low toxicity.

13 Claims, No Drawings

PHARMACEUTICAL COMPOSITION AND METHOD FOR TREATMENT OF PEPTIC ULCER

BACKGROUND OF THE INVENTION

The present invention relates to a pharmaceutical composition and method for the treatment of peptic ulcer.

Peptic ulcer is generally understood to be caused by augmentation of factors which attack the digestive tract wall, such as gastric acid, pepsin or gastric juice excretion, and/or attenuation of factors which act protectively on the digestive tract wall, such as excretion of mucus liquid, resistance of mucosal membrane or mucosal blood perfusion. Taking those factors into consideration, various therapeutic agents have been developed for peptic ulcer and are presently in clinical use. For example, in order to suppress factors which attack mucosal membrane, antacids such as sodium bicarbonate, anti-cholinergics such as atropine sulfate, or antigastrin agents such as oxethazaine are used. For the purpose of augmenting protective factors, such agents as protect or stimulate regeneration of mucus membrane, for example, glutamine, cetraxate or aluminum sucrose sulfate, are used.

SUMMARY OF THE INVENTION

An object of this invention is to provide a pharmaceutical composition for the treatment of peptic ulcer, which contains as an active ingredient 2-N-methyl-1,2,3,4-tetrahydro-9H-dibenzo[a,e]-pyridino[3,4-c]-cycloheptatriene (hereafter referred to as MO-8282) or its pharmaceutically acceptable salt as an active ingredient in association with pharmaceutically acceptable carriers.

Another object of this invention is to provide a method for treating peptic ulcer by using MO-8282 or its pharmaceutically acceptable salt.

DETAILED DESCRIPTION OF THE INVENTION

Under the background stated above, the present invention have carried out an intensive investigation for the purpose of developing an effective therapeutic agent for the treatment of peptic ulcer by using several experimental ulcer models which are widely accepted. The anti-ulcer effect of drugs can be subjectively estimated thereby, and the therapeutic effect of the drug estimated in the studies that employed these models correlates well with clinical efficacy of the drugs.

As a result, the present inventors have found that MO-8282 and its salt possess significant therapeutic effects on peptic ulcer.

MO-8282, which relates to the present invention and has the formula (I),

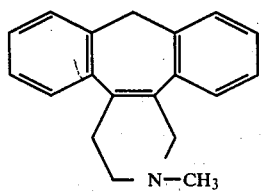

(I)

is a known compound, which has anti-depressive activity, and can be synthesized according to the method of Van der Burg (U.S. Pat. No. 4,002,632) Briefly, 3-(2-Benzylphenyl)-5-carboethoxy-1-methyl-piperidon-4 was mixed with 5 N hydrochloric acid and allowed to react. The reaction mixture was sequentially extracted with benzene, hydrochloric acid and then with ether to obtain a mixture of 3-(2-benzylphenyl)-1-methyl-piperidon-4 and 2-N-methyl-1,2,3,4-tetrahydro-9H-dibenzo-[a,e]-pyridino[3,4-c]-cyclo-heptariene (MO-8282). Polyphosphoric acid was added to this mixture and the mixture was allowed to complete reaction. MO-8282 thus obtained has a molecular weight of 261.5, is colorless plate-like crystals with a melting point of 138.5°–139.5° C., and is soluble in ether, ethyl acetate, n-hexane and chloroform and insoluble in ethanol.

MO-8282 can be converted into a pharmacologically acceptable salt using appropriate acids. For example, the following acids may be used: inorganic acids such as hydrochloric acids, sulfuric acid, nitric acid or phosphoric acid, and organic acids such as acetic acid, maleic acid, lactic acid, tartaric acid, formic acid or oxalic acid. Most commonly, maleic acid is prefered. Maleic acid salt of MO-8282 is obtained by treating free base of MO-8282 with maleic acid dissolved in alcohol. Maleic acid salt of MO-8282 thus obtained has a molecular weight of 377.4, a melting point of 160°–162° C., and is soluble in water or ethanol and stable at room temperature.

Now, the pharmacological action and toxicity of MO-8282 will be described below, with reference to typical experiments.

EXPERIMENT I

Effect on Shay ulcer of rats

A group of 8 Wistar male rats weighing 130–180 g were used in a group. After a 48-hour period of fasting, the pylorus was ligated under ether anesthesia and MO-8282 was administered subcutaneously. Nineteen hours after ligation, the severity of ulcerous lesions in the proventricular part of the stomach was observed and expressed in a numerical scale according to the method of Adami et al. (Arch. Int. Pharmacodyn. Ther., 143, 113 (1964)) as the ulcer-index. Inhibition of ulceration was calculated with ulcer-indexes of the treated group and those of a control group. The anti-ulcer effects of well-known therapeutic agents on the market, sulpiride and cetraxate, were examined for comparison. The results are shown in Table 1.

TABLE 1

| Control | Dose (mg/kg) | Inhibition rate (%) |
| --- | --- | --- |
| Control | — | 0 |
| MO-8282 | 3 | 34.9 |
| MO-8282 | 10 | 44.2 |
| Sulpiride | 100 | 16.3 |
| Cetraxate | 300 | 44.2 |

As shown in Table 1, MO-8282 showed significant inhibitory action on Shay ulcer in rats and its efficacy was superior to the two reference drugs, sulpiride and cetraxate.

EXPERIMENT 2

Effect on histamine-induced ulcer in guinea-pigs

Groups of 10 male guinea-pigs weighing 280–300 g were used. After a 24-hour period of fasting, MO-8282 was orally administered to the animals, and ten minutes after MO-8282 administration, 5 mg/kg of histamine were intravenously injected. Two hours later, the stomach was removed and the size of the ulcerous lesions were measured. Based on the size of the lesions, the inhibitory effect of the drug was estimated. The effects of sulpiride, cetraxate and aluminum sucrose sulphate were also determined for comparison. The results are shown in Table 2.

TABLE 2

| Control | Dose (mg/kg) | Inhibition rate (%) |
| --- | --- | --- |
| Control | — | 0 |
| MO-8282 | 3 | 54.7 |
| MO-8282 | 10 | 98.6 |
| Sulpiride | 300 | 5.6 |
| Cetraxate | 300 | −7.0 |
| Aluminum sucrose sulphate | 1,000 | 98.3 |

As shown in Table 2, MO-8282 showed significant inhibitory action on histamine-induced ulcers in guinea-pigs and its efficacy was superior to that of the reference drugs.

EXPERIMENT 3

Effect on acetic acid-induced ulcer in rats

Groups of 14–16 male Wistar rats weighing 210–280 g were used. According to the method of Okabe et al. (Folia Pharmacologica Japonica, 74, 773 (1978)), 0.015 ml of 20% acetic acid solution was injected under the serous membrane at the border of the proventricular part and glandular part of the stomach. Then the abdomen was closed and MO-8282 was administered orally three times a day for 10 days. The stomach was removed 12 days after the injection of acetic acid and the size of the ulcerous lesions was measured. Based on the size of the lesions, the inhibitory effect of the drug was estimated. The effects of sulpiride were also determined for comparison. The results are shown in Table 3.

TABLE 3

| Control | Dose (mg/kg) | Inhibition rate (%) |
| --- | --- | --- |
| Control | — | 0 |
| MO-8282 | 3 | 23.2 |
| MO-8282 | 10 | 51.2 |
| Sulpiride | 100 | 43.9 |

As shown in Table 3, MO-8282 showed significant inhibitory action on acetic acid-induced ulcer in rats and its efficacy was superior to that of the reference drug with a lower dose. Furthermore, promotion of healing by the compound was also evident under microscopic observation.

EXPERIMENT 4

Acute toxicity

Acute oral toxicity of MO-8282 was investigated using ICR mice and Wistar rats. $LD_{50}$ was calculated by the Litchfield-Wilcoxon method using mortality at 7 days after drug administration. The results are shown in Table 4.

| Animal | Sex | $LD_{50}$ (mg/kg) |
| --- | --- | --- |
| ICR mice | male | 423 |
| ICR mice | female | 454 |
| Wistar rats | male | 630 |
| Wistar rats | female | 554 |

As shown in Table 4, the toxic dose of MO-8282 was shown to be considerably higher than its therapeutic dose, and the fact that MO-8282 is a highly safe therapeutic agent was demonstrated.

As has been described in the above experiments, MO-8282 is highly effective as a therapeutic agent for peptic ulcer.

Although the daily dose of MO-8282 as a therapeutic agent for peptic ulcer in humans is in the range of from 1.0 to 100 mg, preferably from 1.5 to 60 mg, it may be suitably increased or decreased depending on the symptoms, sex and age of the patient.

Although the agent of the present invention is generally prepared in the form of an oral agent, for example tablets, capsules, granules, powders and liquid oral preparations, it may be used in other forms of preparation such as rectal suppositories.

The compound of this invention, MO-8282, can be formulated into agents by any of the conventional methods using pharmaceutically acceptable carriers or excipients. Examples of solid carriers and excipients usable advantageously herein include common excipients such as lactose, mannitol, corn starch and potato starch; binders such as crystalline cellulose, cellulose derivatives, arabic gum, corn starch and gellatin; disintegrators such as corn starch, potato starch and calcium carbohydroxymethylcellulose; and lubricants such as talc and magnesium stearate. Examples of liquid carriers usable advantageously herein include distilled water for injection, physiological saline solution, vegetable oils for injection and glycols such as propylene glycol and polyethylene glycol.

Some typical but non-limiting formulations of the agent of this invention will be shown below.

Formulation 1 (Tablets)

One hundred grams of MO-8282, 720 g of lactose, 150 g of potato starch, 15 g of polyvinyl alcohol and 15 g of magnesium stearate were weighed. Such amounts of MO-8282, lactose and potato starch were mixed until the mixture became homogeneous. Then an aqueous solution of the polyvinyl alcohol was added to the mixture and granulated by a wet granulation process. The granules thus obtained were dried and mixed with the above-mentioned amount of magnesium stearate and formed into tablets, each weighing 200 mg.

Formulation 2 (Capsules)

One hundred grams of MO-8282, 885 g of lactose and 15 g of magnesium stearate were mixed until the mixture became homogeneous. Then the mixture was filled into #3 hard gellatin-capsules, so that each capsule contained 100 mg of the mixture.

Formulation 3 (10% powder)

One hundred grams of MO-8282, 890 g of lactose and 10 g of magnesium stearate were mixed until the mixture became homogeneous to obtain a 10% powder preparation.

What is claimed is:

1. A method for treating a patient suffering from peptic ulcer, comprising administering an amount therapeutically effective agent peptic ulcer of an agent comprising 2-N-methyl-1,2,3,4-tetrahydro-9H-dibenzo[a,e]pyridino[3,4-c]-cycloheptatriene (MO-8282) or its pharmaceutically acceptable salt to said patient.

2. A method according to claim 1, wherein the pharmaceutically acceptable salt is maleic acid salt.

3. A method according to claim 1 or 2, wherein said agent is administered in the form of an oral preparation.

4. A method according to claim 1 or 2, wherein said agent is administered in the form of a rectal suppository.

5. A method according to claim 1 or 2, wherein said agent is administered in the form of an injection.

6. A method according to claim 1 or 2, wherein the daily administration dose of MO-8282 is in a range of 1 to 100 mg.

7. A method according to claim 3, wherein the daily administration dose of MO-8282 is in a range of 1 to 100 mg.

8. A method according to claim 4, wherein the daily administration dose of MO-8282 is in a range of 1 to 100 mg.

9. A method according to claim 5, wherein the daily administration dose of MO-8282 is in a range of 1 to 100 mg.

10. A method according to claim 6, wherein the daily administration dose of MO-8282 is in a range of 1.5 to 60 mg.

11. A method according to claim 7, wherein the daily administration dose of MO-8282 is in a range of 1.5 to 60 mg.

12. A method according to claim 4, wherein the daily administration dose of MO-8282 is in a range of 1.5 to 60 mg.

13. A method according to claim 5, wherein the daily administration dose of MO-8282 is in a range of 1.5 to 60 mg.

* * * * *